US00PP15348P2

(12) United States Plant Patent
Klemm

(10) Patent No.: US PP15,348 P2
(45) Date of Patent: Nov. 23, 2004

(54) ***CALIBRACHOA* PLANT NAMED 'KLEC02072'**

(50) Latin Name: ***Calibrachoa* sp.**
Varietal Denomination: KLEC02072

(75) Inventor: Nils Klemm, Stuttgart (DE)

(73) Assignee: Klemm & Sohn GmbH & Co. KG., Stuttgart (DE)

( * ) Notice: Subject to any disclaimer, the term of this patent is extended or adjusted under 35 U.S.C. 154(b) by 0 days.

(21) Appl. No.: 10/783,366

(22) Filed: Feb. 21, 2004

(51) Int. Cl.[7] ..... A01H 5/00
(52) U.S. Cl. ..... Plt./263
(58) Field of Search ..... Plt./263

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Calibrachoa* plant named 'KLEC02072', characterized by its cascading plant habit; freely branching habit; early flowering habit; red-colored flowers; and good weather tolerance.

1 Drawing Sheet

Botanical classification/cultivar designation: *Calibrachoa* sp. cultivar KLEC02072.

BACKGROUND OF THE INVENTION

The present Invention relates to a new and distinct cultivar of *Calibrachoa* plant, botanically known as *Calibrachoa* sp., and hereinafter referred to by the name 'KLEC02072'.

The new *Calibrachoa* is a product of a planned breeding program conducted by the Inventor in Stuttgart, Germany. The objective of the program is to create new early-flowering *Calibrachoa* cultivars with compact and cascading growth habit, freely branching habit and attractive flower colors.

The new *Calibrachoa* originated from a cross-pollination made by the Inventor during the summer of 1999 of a proprietary selection of *Calibrachoa* identified as code number S 14, not patented, as the female, or seed, parent with a proprietary selection of *Calibrachoa* identified as code number S 52, not patented, as the male, or pollen, parent. The new *Calibrachoa* was selected by the Inventor in May, 2000 in a controlled environment in Stuttgart, Germany from within the resulting progeny from the cross-pollination.

Asexual reproduction of the new cultivar by terminal cuttings taken in a controlled environment in Stuttgart, Germany since May, 2000, has shown that the unique features of this new *Calibrachoa* are stable and reproduced true to type in successive generations.

SUMMARY OF THE INVENTION

Plants of the cultivar KLEC02072 have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'KLEC02072'. These characteristics in combination distinguish 'KLEC02072' as a new and distinct cultivar of *Calibrachoa*:

1. Cascading plant habit.
2. Freely branching habit.

3. Early flowering habit.
4. Red-colored flowers.
5. Good weather tolerance; tolerant to rain and wind and high and low temperatures.

Plants of the new *Calibrachoa* have a more trailing plant habit than plants of the female parent selection. Plants of the new *Calibrachoa* and the male parent selection differ in flower coloration as flowers of plants of the male parent selection were pink in color.

Plants of the cultivar KLEC02072 can be compared to plants of the *Calibrachoa* cultivar Sunbelchipi, disclosed in U.S. Plant Pat. No. 10,355. However, in side-by-side comparisons conducted in Stuttgart, Germany, plants of the new *Calibrachoa* and the cultivar Sunbelchipi, differed primarily in flower color as plants of the cultivar Sunbelchipi had cherry red-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Calibrachoa*.

The photograph comprises a side perspective view of typical plants of 'KLEC02072' grown in a hanging basket container.

DETAILED BOTANICAL DESCRIPTION

Plants used in the aforementioned photograph and following description were grown under conditions that closely approximate commercial production conditions during the spring in Stuttgart, Germany in a glass-covered greenhouse. Plants were about five months old from planting rooted cuttings. During the production of the plants, day and night temperatures ranged from 16 to 18° C. and light levels were about 20,000 lux. Plants grown in 12-cm containers were used for the description. In the description, color references are made to The Royal Horticultural Society Colour Chart, 1995 Edition, except where general terms of ordinary dictionary significance are used.

Botanical classification: *Calibrachoa* sp. cultivar KLEC02072.

Parentage:

*Female, or seed, parent.*—Proprietary selection of *Calibrachoa* sp. identified as S 14, not patented.

*Male, or pollen, parent.*—Proprietary selection of *Calibrachoa* sp. identified as S 52, not patented.

Propagation:

*Type cutting.*—Terminal vegetative cuttings.

*Time to initiate and develop roots.*—Summer: About 21 days at 20 to 26° C. Winter: About 28 days at 20° C.

*Root description.*—Fine, fibrous and white in color.

*Root habit.*—Freely branching.

Plant description:

*Form.*—Annual flowering plant; initially upright to semi-upright then cascading; uniform flattened mounded appearance.

*Usage.*—Appropriate for hanging baskets, window boxes and patio containers.

*Plant height* (*from soil level to top of plant plane*).—About 8 cm.

*Plant diameter* (*area of spread*).—About 60 cm.

*Growth rate.*—Moderate.

*Branching habit.*—Freely branching, about four to five lateral branches per plant; pinching is typically not required.

*Lateral branch description.*—Length: About 30 cm. Diameter: About 3 mm. Internode length: About 0.5 to 2 cm. Texture: Glabrous. Color: 145A.

*Foliage description.*—Leaves simple, generally symmetrical and long persisting; sessile. Arrangement: Alternate. Length: About 1 to 3 cm. Width: About 0.5 to 1 cm. Shape: Lanceolate to elliptic. Apex: Acute. Base: Attenuate. Margin: Entire. Texture, upper and lower surfaces: Smooth, glabrous. Venation pattern: Pinnate. Color: Developing and fully expanded foliage, upper surface: 138A. Developing and fully expanded foliage, lower surface: 138B. Venation, upper surface: 138A. Venation, lower surface: 138C.

Flower description:

*Flower type and habit.*—Flowers face somewhat upright or outward; single, axillary; salverform. Flowers not persistent. Freely flowering habit, about eight to ten open flowers and about 15 to 25 flower buds per lateral stem. Flowers not fragrant.

*Natural flowering season.*—Spring until frost in the autumn; flowering continuous during this time.

*Time to flower.*—Early flowering; plants begin flowering about 12 weeks after planting.

*Flower longevity on the plant.*—About seven days.

*Flower size.*—Diameter: About 3.5 cm. Tube length: About 1.7 cm. Throat diameter, distal end: About 8 mm. Tube diameter, proximal end: About 2 mm.

*Flower buds.*—Length: About 1.3 cm. Diameter: About 4 mm. Shape: Irregular, oblong. Color: 150B.

*Corolla.*—Arrangement/appearance: Single whorl of five petals, fused into flared trumpet. Petal length from throat: About 1.5 cm. Petal width: About 1.4 cm. Petal shape: Roughly spatulate; slightly recurved. Apex: Crenate. Petal margin: Entire. Petal texture, upper and lower surfaces: Smooth, glabrous. Color: Petal, when opening, upper surface: 46B. Petal, when opening, lower surface: 54A. Petal, fully opened, upper surface: 45C; venation, 53A. Petal, fully opened, lower surface: 54A; venation, 59A. Flower throat (inside): 12A; venation, 59B. Flower tube (outside): 45C; venation, 187A.

*Sepals.*—Arrangement/appearance: Single whorl of five sepals; calyx, star-shaped. Length: About 1.7 cm. Width: About 6 mm. Shape: Lanceolate to elliptic. Apex: Acute. Margin: Entire. Texture, upper and lower surfaces: Smooth, glabrous, glossy. Color, upper surface: 136B. Color, lower surface: 136C.

*Peduncles.*—Length: About 1.5 to 2 cm. Width: About 2 mm. Strength: Moderately strong. Angle: Erect to about 75° from vertical. Texture: Glabrous, smooth. Color: 144A.

*Reproductive organs.*—Stamens: Quantity: Six per flower. Anther shape: Elliptic. Anther length: About 1 to 2 mm. Anther color: 11B. Pollen amount: Scarce. Pollen color: 11B. Pistils: Quantity: One per flower. Pistil length: About 7 mm. Stigma shape: Oval. Stigma color: 149A. Style length: About 5 mm. Style color: 150A. Ovary color: 154A.

*Seed/fruit.*—Seed and fruit production has not been observed.

Disease/pest resistance: Plants of the new *Calibrachoa* have been noted to be resistant to Powdery Mildew. Plants of the new *Calibrachoa* have not been noted to be resistant to other pathogens and pests common to *Calibrachoas.*

Weather/temperature tolerance: Plants of the new *Calibrachoa* are tolerant to rain and wind and have been observed to tolerate temperatures from 1 to 50° C.

It is claimed:

1. A new and distinct cultivar of *Calibrachoa* plant named 'KLEC02072', as illustrated and described.

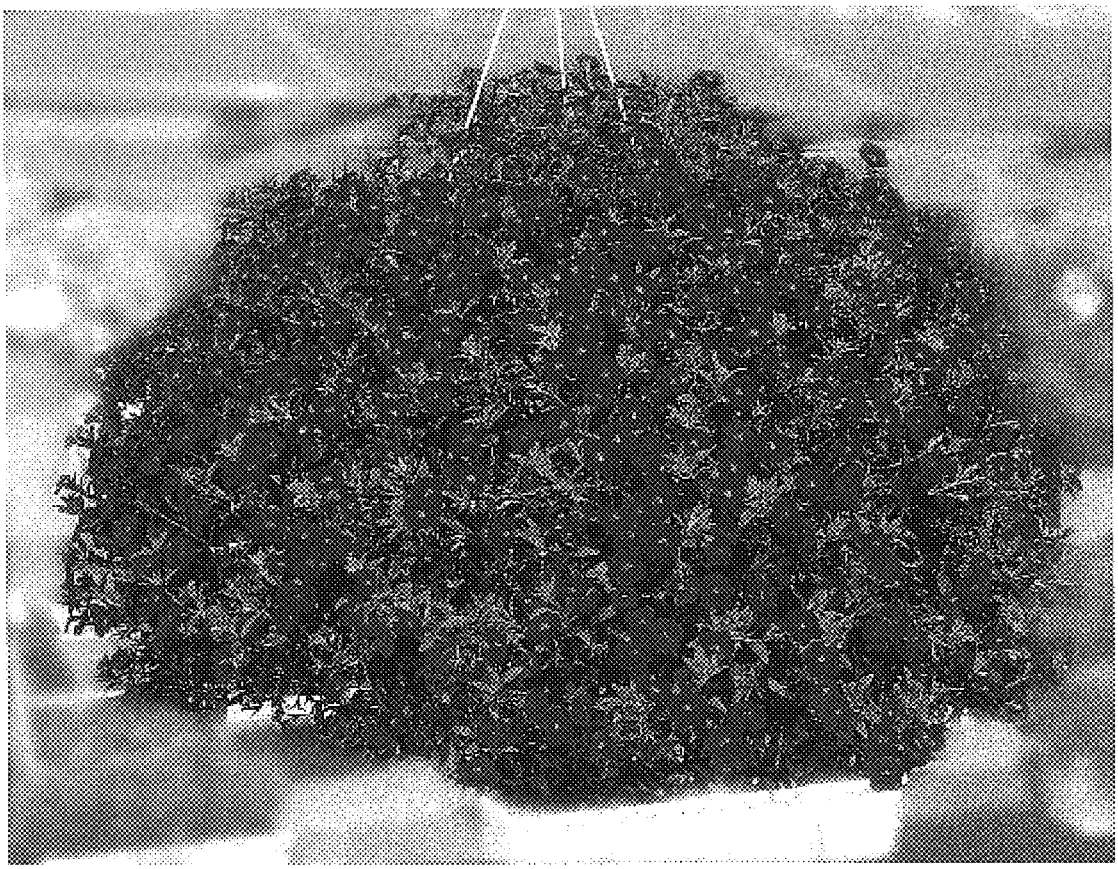

* * * * *